United States Patent
Lajtai et al.

(10) Patent No.: US 7,553,297 B2
(45) Date of Patent: Jun. 30, 2009

(54) ACCESS CANNULA FOR ENDOSCOPIC OPERATIONS

(75) Inventors: Georg Lajtai, Wels (AT); Michael Sauer, Tuttlingen (DE); Andre Timmermans, Ruurlo (NL)

(73) Assignee: Karl Storz GmbH & Co. KG (DE)

( * ) Notice: Subject to any disclaimer, the term of this patent is extended or adjusted under 35 U.S.C. 154(b) by 341 days.

(21) Appl. No.: 10/320,308

(22) Filed: Dec. 16, 2002
(Under 37 CFR 1.47)

(65) Prior Publication Data

US 2003/0181858 A1    Sep. 25, 2003

Related U.S. Application Data

(63) Continuation of application No. 10/172,047, filed on Jun. 14, 2002, now abandoned.

(51) Int. Cl.
*A61M 5/178*    (2006.01)
(52) U.S. Cl. .................................. 604/167.06
(58) Field of Classification Search ............. 604/264, 604/272, 523, 528, 533, 166.01, 164.09–164.13, 604/95.01, 93.01, 164.02, 167.01–167.06, 604/236–238, 244–247, 537
See application file for complete search history.

(56) References Cited

U.S. PATENT DOCUMENTS

| | | | |
|---|---|---|---|
| 4,430,081 A * | 2/1984 | Timmermans | 604/256 |
| 5,009,391 A * | 4/1991 | Steigerwald | 251/149.1 |
| 5,234,455 A * | 8/1993 | Mulhollan | 606/191 |
| 5,364,372 A | 11/1994 | Danks et al. | 604/264 |
| 5,383,860 A * | 1/1995 | Lau | 604/167.03 |
| 5,423,762 A * | 6/1995 | Hillstead | 604/167.04 |
| 5,800,451 A | 9/1998 | Buess et al. | 606/185 |
| 5,820,606 A * | 10/1998 | Davis et al. | 604/256 |
| 5,944,697 A * | 8/1999 | Biche | 604/174 |
| 5,957,888 A | 9/1999 | Hinchliffe | 604/117 |
| 6,120,480 A * | 9/2000 | Zhang et al. | 604/164.01 |

FOREIGN PATENT DOCUMENTS

WO    WO 01/08563    2/2001

* cited by examiner

*Primary Examiner*—Nicholas D Lucchesi
*Assistant Examiner*—Theodore J Stigell
(74) *Attorney, Agent, or Firm*—St. Onge Steward Johnston & Reens LLC

(57) ABSTRACT

An access cannula for endoscopic operations comprises a cannula tube, a valve body unit having a valve housing and a valve mounted in the valve housing. The valve body can be connected releasably as a completely assembled valve body unit to one end of the cannula tube. The valve of the valve body ensures a tight closure of the cannula tube at said one end, but allows an instrument to be passed through the valve body unit and the cannula.

14 Claims, 5 Drawing Sheets

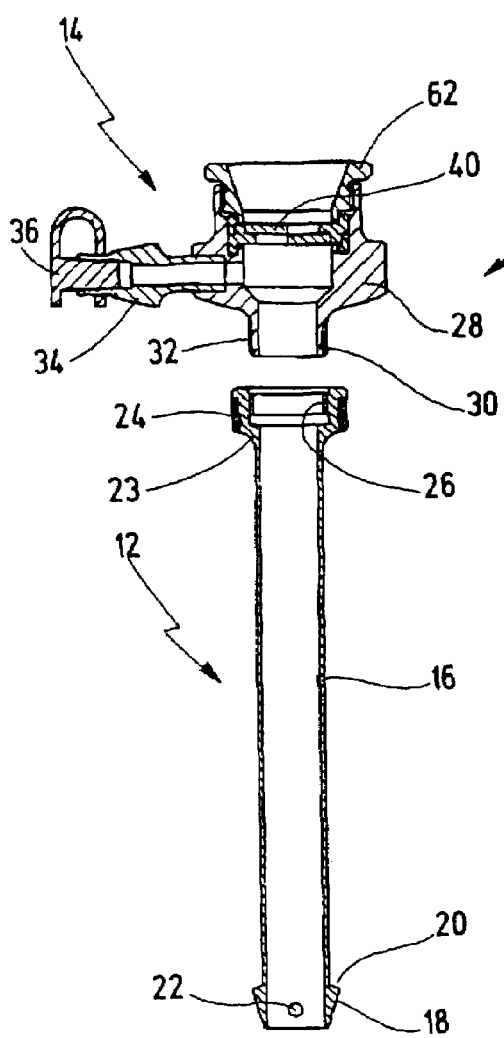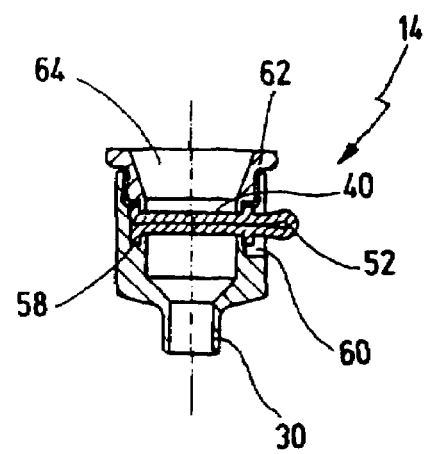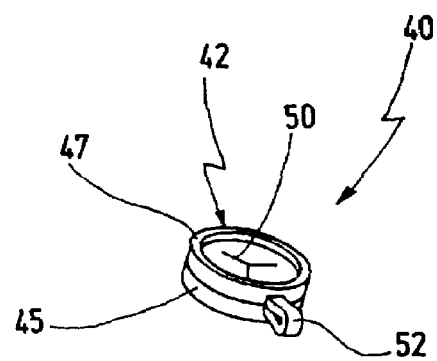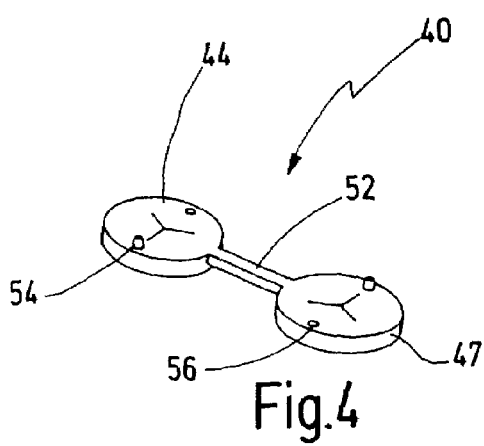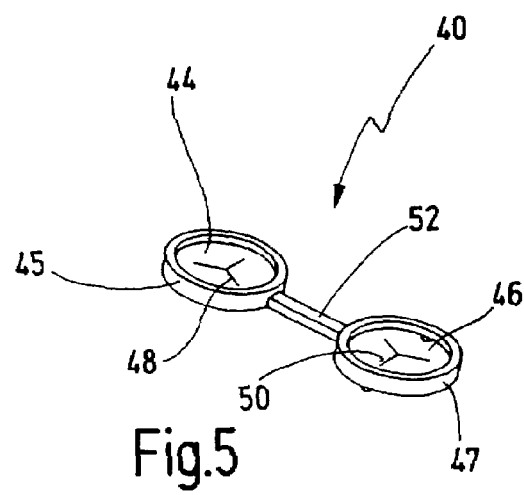
Fig.1
Fig.2
Fig.3
Fig.4
Fig.5

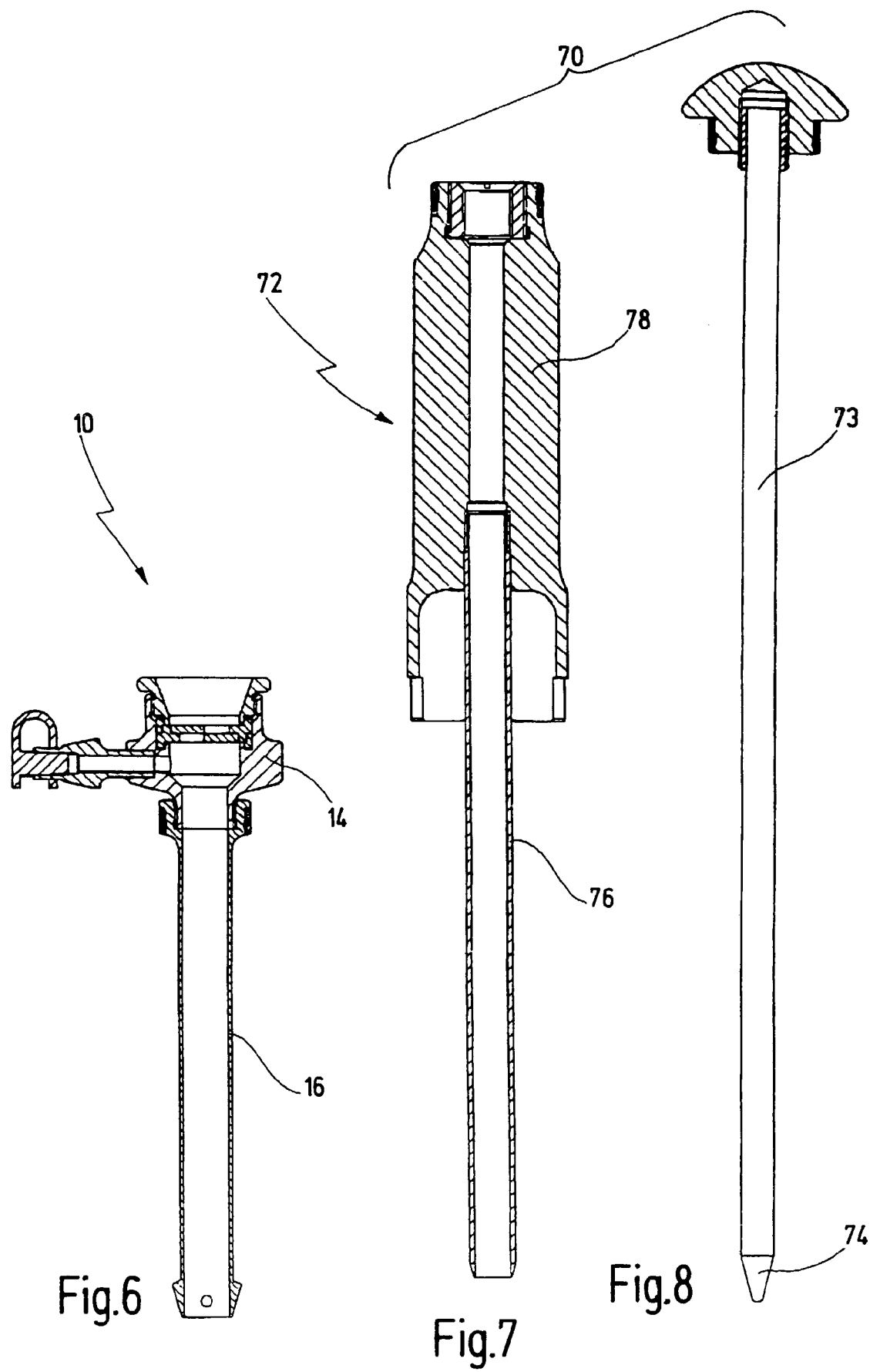

ACCESS CANNULA FOR ENDOSCOPIC OPERATIONS

CROSS REFERENCE TO RELATED APPLICATIONS

This is a continuation of U.S. patent application Ser. No. 10/172,047, filed Jun. 14, 2002 now abandoned.

The invention relates to an access cannula for endoscopic operations, in particular for arthroscopy.

Access cannulas for endoscopic operations are generally known.

In minimally invasive operating techniques, whose application is becoming ever more widespread, such an access is provided using a trocar. A trocar has a sleeve-like or cannula-like hollow tubular body which is introduced into the body, for example through the abdominal wall, in order to perform operations within the peritoneal space. Suitable instruments, for example endoscopes, are then guided through the trocar in order to be able to visually monitor the operation being performed inside the body.

To bring the trocar in place, a pointed trocar mandrel or core rod is inserted into the trocar sleeve and a skin incision is made in order to introduce the access cannula, in this case the trocar sleeve, into the body.

In minimally invasive operations on soft tissue parts, for example through the abdominal wall, the trocar can be introduced exactly in the required size.

But it is much more difficult to create an access in arthroscopic procedures. If a minimally invasive endoscopic operation is to be performed in a joint, the spaces between two bones forming a joint are often very small, with the result that a trocar cannot easily be fitted using the technique described above.

It is often desirable or even necessary to arrange a plurality of access cannulas in the operating field in order either to observe the operating field from a plurality of directions or to obtain an access to the joint from a plurality of directions.

A further problem is that, to permit better viewing of the operating site through the access cannula, gases and/or liquids are introduced in order to slightly expand the body in the operating site by means of overpressure. Irrigation fluids are often also passed through the access cannula. To prevent body fluids, gases or irrigation fluids from running out from the proximal end of the access cannula, a valve is usually provided there which, on the one hand, ensures a tight closure of the cannula tube but, on the other hand, also provides for the possibility of pushing instruments or endoscopes through the valve. Various configurations of valves with flaps or with slit seals are known for this purpose.

On account of the aforementioned widespread application of minimally invasive surgery, a large number of access cannulas are required which then have to be properly cleaned and sterilized after the surgery, which necessitates the use of high-quality materials.

It is therefore the object of the present invention to make available an access cannula for endoscopic operations which permits different operating methods and different possibilities of bringing the cannula in place, and which can be produced inexpensively, but nevertheless functions effectively and safely during the intervention.

SUMMARY OF THE INVENTION

The object is achieved by an access cannula which has a cannula tube and a valve housing, which valve housing can be connected releasably to one end of the cannula tube, said valve housing having a valve which ensures a tight closure of the cannula tube at the end but allows instruments to be passed through the cannula tube, and wherein said valve housing is designed as an entire valve body unit, which entire unit is releasable connected to the cannula.

It is now possible, with one and the same valve body unit, to combine different cannula tubes which are best suited for the particular operating technique. At the same time, this affords the possibility of initially inserting just the cannula tube, and only later securing the entire valve body unit to the latter. This also makes it possible to fit a plurality of cannula tubes which lie close to one another, and are of a very slender construction, without the relatively voluminous valve body being present at the same time. A very high degree of flexibility is thus obtained. It is only when the actual operation is performed, that is to say after the preparation involving placement of the access cannula, that the valve body unit need be connected to the cannula tube and thus ensure a tight closure of this end of the cannula tube. The instruments, for example endoscopes or surgical instruments, can then be pushed through the valve body itself.

Increased flexibility is also achieved by the fact that other instruments can also be attached for a time to the cannula tube, for which purpose the entire valve body unit is simply removed and an instrument, e.g. a viewing optic or the like, can be attached for a time.

It is therefore also possible, depending on the objective and on the operating technique, to arrange different cannula tubes on a single type of a valve body unit which has standardized couplings for other instruments.

This not only increases flexibility but also ensures a considerable reduction in cost and guarantees a perfect sealing. The releasable connection between valve body unit and cannula tube can be effected in different ways, for example by means of a screw connection, a bayonet lock, a snap-fit connection, etc.

In a further embodiment of the invention, the valve housing is designed as a sterilizable component part which can be used a number of times.

This measure has the advantage that the aforementioned configuration affords the possibility of producing the valve housing as a high-quality component part, for example made of medical grade steel, which can be sterilized and can be used a number of times.

In a further embodiment of the invention, the cannula tube is designed as a disposable component part.

This measure, in particular together with the aforementioned measure, has the advantage that the cannula tube can be produced as an inexpensive disposable part for single use, to which the reusable valve body unit can then be coupled.

In a further embodiment of the invention, the valve is designed as a double-disk valve.

This measure has the advantage that, by means of the double-disk construction, an instrument has to be guided through two disks, which ensures particularly reliable sealing.

In a further embodiment of the invention, a slit seal is provided in each disk.

This measure has the advantage that instruments of different diameter can be guided through, with a tight closure being ensured in each case. This is especially the case because the valve is designed as a double-disk valve.

In a further embodiment of the invention, the slits are designed in a star shape, and the slits of the two disks are offset in relation to one another.

This measure contributes still further to the excellent tight closure.

In a further embodiment of the invention, the two disks are connected to one another via an elastic bridge.

This measure has the considerable advantage that the double-disk valve consists only of one component part.

In a further embodiment of the invention, locking means are provided on the disks and serve to lock the disks onto one another.

This measure has the advantage that the double-disk valve can be produced as a body which extends in one plane and in which the two disks are connected to one another via the bridge and, for assembly, are turned back and placed one upon the other, by bending the bridge, and are then held firmly on one another by the locking means.

In a further embodiment of the invention, the valve housing is designed in two parts, and the valve can be arranged between the two parts.

This measure has the advantage that the valve is held in the valve housing by structurally simple means. This measure also permits simple dismantling of the valve housing for cleaning and sterilizing.

In a further embodiment of the invention, the valve housing has a main body which has a neck for releasable connection to the cannula tube and moreover has a recess into which the valve can be inserted, the valve being fixed via a clamping ring.

This measure has the advantage that the main body of the valve housing and the clamping ring can be made from high-quality special steel materials, whereas the interposed valve can be made as a disposable part. For this reason, only these two parts need to be sterilized, and a new valve can be inserted after sterilization.

This increases the versatility still further and also contributes to a cost reduction. In this case, both the cannula tube and the valve can be designed as a disposable part, and only the two-part valve housing is made of high-quality and precision-finished materials.

In a further embodiment of the invention, the cannula tube has, at the distal end, a ring which widens conically in the proximal direction.

This measure has the advantage that the cannula tube can be pushed via this ring into the joint, specifically in arthroscopic operations, and secured against removal or inadvertent loosening during the operation since the distal tip with the conical ring is as it were snapped into the joint.

In a further embodiment of the invention, the cannula tube is designed as a component part of a trocar device.

This measure has the advantage that it permits a flexible attachment to different trocars, for example for adults, for children, for thin and for thickset individuals.

In a further embodiment of the invention, the trocar device has a mandrel with a hand grip and also a core rod, which mandrel can be introduced into the cannula tube.

This measure has the advantage that the access cannula is designed as it were as a trocar sleeve which is introduced into the body together with the mandrel and core rod.

In a further embodiment of the invention, the cannula tube is designed as a component part of a dilatation device.

This measure has the considerable advantage that, upon access, dilatation can be performed without causing trauma. For example in arthroscopic operations, a first access is initially made with very thin cannulas, this access is then widened by pushing on dilatation rods of ever increasing diameter, and, finally, the access cannula according to the invention is fitted as an operating cannula which remains in the body.

For this purpose, the dilatation device particularly advantageously has a puncture needle, a guide wire, at least one dilatation mandrel for attachment onto the guide wire, the cannula tube being designed in such a way that it can be pushed onto a dilatation mandrel.

This arrangement is of advantage particularly in terms of the atraumatic placement of the cannula tube for an arthroscopic operation, this versatility having an especially favorable effect in this case. The guide tube can be pushed onto the dilatation mandrel again by means of the mandrel provided with a hand grip.

It will be appreciated that the features mentioned above and those still to be discussed below can be used not only in the respective combination mentioned but also in other combinations or in isolation, without departing from the scope of the present invention.

BRIEF DESCRIPTION OF THE DRAWINGS

The invention is described and explained in greater detail below on the basis of a number of selected illustrative embodiments and with reference to the attached drawings, in which:

FIG. 1 shows a longitudinal section through an access cannula according to the invention, consisting of cannula tube and valve body unit, in an exploded view;

FIG. 2 shows a cross section through the valve body unit, turned through 90° about the axis of the cannula tube;

FIG. 3 shows a perspective view of the valve incorporated in the valve housing;

FIG. 4 shows the double-disk valve from FIG. 3 in the opened-out state before being fitted in the valve housing;

FIG. 5 shows a corresponding perspective view of the valve turned through 180°;

FIG. 6 shows a longitudinal section, corresponding to FIG. 1, of the cannula tube and valve body unit when fitted together;

FIG. 7 shows a mandrel, with hand grip, of a trocar device;

FIG. 8 shows a core rod of a trocar device which is intended to cooperate with an access cannula according to the invention in FIG. 6;

DETAILED DESCRIPTION OF PREFERRED EMBODIMENTS

Figure 9:
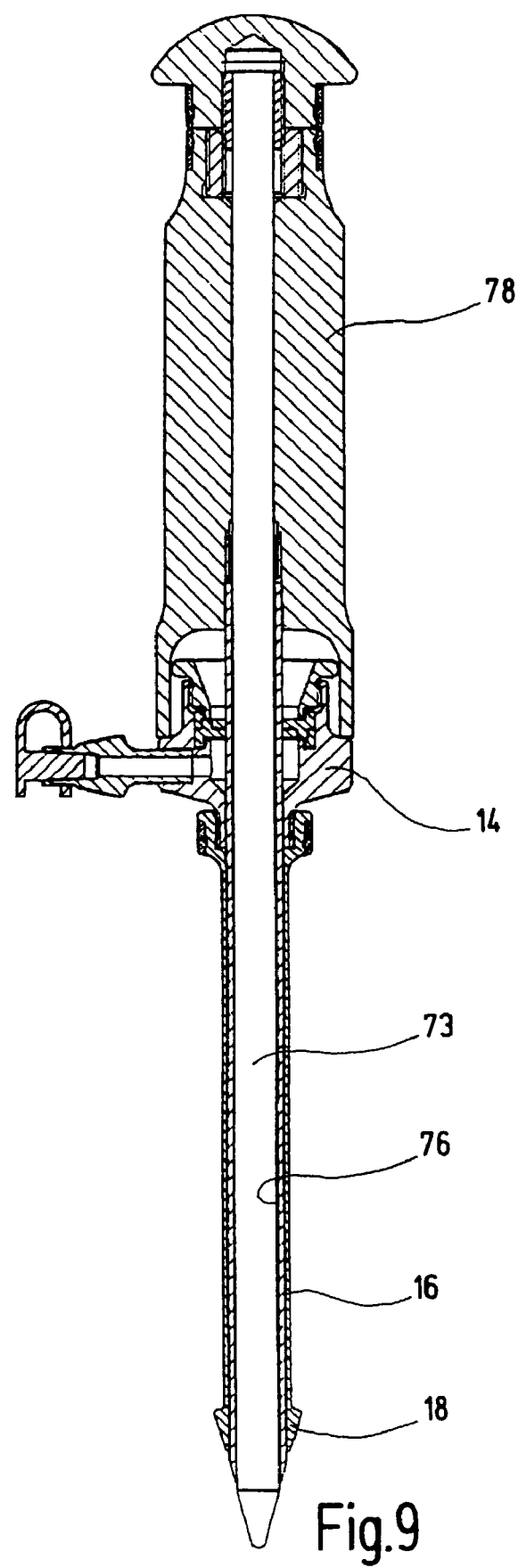
FIG. 9 shows the component parts from FIGS. 6, 7 and 8 when fitted together.

An access cannula shown in FIG. 1 is provided overall with the reference number 10.

The access cannula 10 consists of a cannula tube 12 and of a valve body unit 14.

The cannula tube 12 has a tube 16 at whose distal end a conical ring 18 is provided as nose. The conicity is chosen such that the ring 18 widens as viewed from distal to proximal.

A shoulder 20 is thus created at a distance from the distal end. This ring 18 serves to be driven into a body opening, for example into a joint, and is then locked therein in order to secure against removal of the cannula tube 12.

Provided in the area of the conical ring 18, in the lateral wall, there is a through-opening 22 which serves to permit pressure compensation with the environment during operations. At the end 23 remote from the conical ring 18, the tube 16 is provided with a collar 24 of greater diameter which has an internal thread 26.

The valve body unit 14 is designed as a two-part valve housing. One part is provided by a main body 28 from one side of which there protrudes a tubular neck 30, which is provided with an external thread 32. The external thread 32 is configured such that it can be turned into the internal thread 26 in the collar 24 of the tube 16. The clear internal diameter of the neck 30 corresponds to the clear internal diameter of the tube 16. Protruding laterally from the main body 28 there is an attachment piece 34 which is closed by a cap 36. This lateral attachment piece 34 is used to deliver fluids or gases laterally via the valve body unit 14 to the tube 16 or to remove them from it.

A valve 40 is arranged in the valve body unit 14, proximally of the lateral attachment piece 34. The valve 40 thus ensures a tight closure of the valve body unit 14 in the proximal direction and of the cannula tube 12 when the valve body unit 14 is connected to it via the screw connection.

The valve 40 in this case consists of a double-disk valve 42, as can be seen in particular from FIGS. 2 through 5.

The double-disk valve 42 has two disks 44 and 46, each surrounded by a ring 45 and 47, respectively. A star-shaped slit 48, 50 with three arms is provided in each disk 44, 46 respectively. The material of the double-disk valve is a rubber-elastic synthetic material so that, despite the presence of the slits 48 and 50, a tight closure is guaranteed by each disk 44 and 46.

The two rings 45 and 47 are connected to one another via a flexible bridge 52. From the perspective views in FIGS. 4 and 5, it will be seen that the slits 48 and 50 are cut so as to be offset in relation to one another.

As will be seen in particular from FIG. 4, a stud 54 projects from each disk and can be fitted into a corresponding opening 56 on the other disk, in order to provide locking means on the disks serving to lock the two disks one to another.

The double-disk valve 42, in the configuration represented in FIGS. 4 and 5, can thus be produced as a shaped part or punched-out part, and it is later brought into the position shown in FIG. 3 by bending it about the bridge 52.

The valve 40 is inserted into a recess 58 in the main body 28 of the valve body unit 14, the latter having a lateral slot opening 60 from which the bent bridge 52 can laterally extend. The valve 40 is held on the valve body unit 14 via a clamp ring 62, which provides a second part of the two-part valve housing. The clamp ring 62 is provided with an external thread which can be turned into an internal thread (not specifically shown) in the recess 58. The clamping ring 62 then presses the two rings 45 and 47 of the disks 44 and 46 tightly against one another so that a tight closure of the valve body unit 14 is guaranteed by the valve 40 as a whole. The two parts, i.e. main body 28 and clamp ring 62, provide the two-part valve housing.

Inside the valve body unit 14 there is a through-opening 64 whose clear internal diameter is greater than the clear internal diameter of the tube 16, so that for example instruments, e.g. endoscopes or the like, can then be attached to the valve body unit 14.

In FIG. 6, the access cannula 10 is shown in the assembled state, i.e. the valve body unit 14 is mounted in place and ready, i.e. the valve 40 is fitted, and the valve body unit 14 is screwed via its external thread 32 on the neck 30 into the internal thread 26 on the collar 24 of the cannula tube 12.

In this state, the access cannula 10 can for example be a structural part or component part of a trocar device 70, as is shown in FIGS. 7 and 8.

The trocar device 70 thus has a mandrel 72 and a core rod 73 which has a sharpened tip 74.

The mandrel 72 has a hand grip 78 from which a tubular sleeve 76 projects.

The external diameter of the sleeve 76 is chosen such that this corresponds to the clear internal diameter of the tube 16 of the access cannula 10.

The trocar device 70 is shown in its assembled state in FIG. 9, i.e. the core rod 73 is pushed into the sleeve 76 of the mandrel 72, and this assembly is in turn pushed into the cannula tube 12.

From the view in FIG. 9, it will be seen that the tip 74 extends slightly beyond the sleeve 76, and the latter in turn extends beyond the conical ring 18 and is provided with a corresponding conical bevel. This results in the insertion end of the trocar device 70 having a pointed cone shape.

To insert the access cannula 10, which now functions as a trocar sleeve, the core rod 73 is applied to a skin incision and pushed into the body, and the whole assembly in FIG. 9 is driven to the desired depth into the body. The hand grip 78 facilitates this procedure. Mandrel 72 and core rod 73 are then removed. By virtue of the valve body unit 14 with the closed valve 40, it is possible to prevent the escape of body fluids or the like.

It is also possible to initially insert the cannula tube 12 into the body without having the valve body unit 14 mounted, and to screw the valve body unit 14 later onto it.

As has already been described, it is also possible to drive the assembly, as shown in FIG. 6, into place and, after removal of mandrel 72 and core rod 73, if necessary to remove the valve body unit 14 for a short time in order, for example, to fit a second access cannula in the immediate proximity.

This affords a particularly high degree of versatility.

After removal of the access cannula 10, the valve body unit 14 can be dismantled, cleaned and sterilized, and, depending on its design, the double-disk valve 42 can likewise be cleaned and reinserted or can be replaced by another one.

Depending on its design, the cannula tube 12 can also be cleaned and sterilized, or it can also be made as a disposable part and discarded after the operation. The cleaned, sterilized and reassembled valve body unit 14 can then be again connected to a cannula tube 12.

Figures 10, 11, 12, 13:
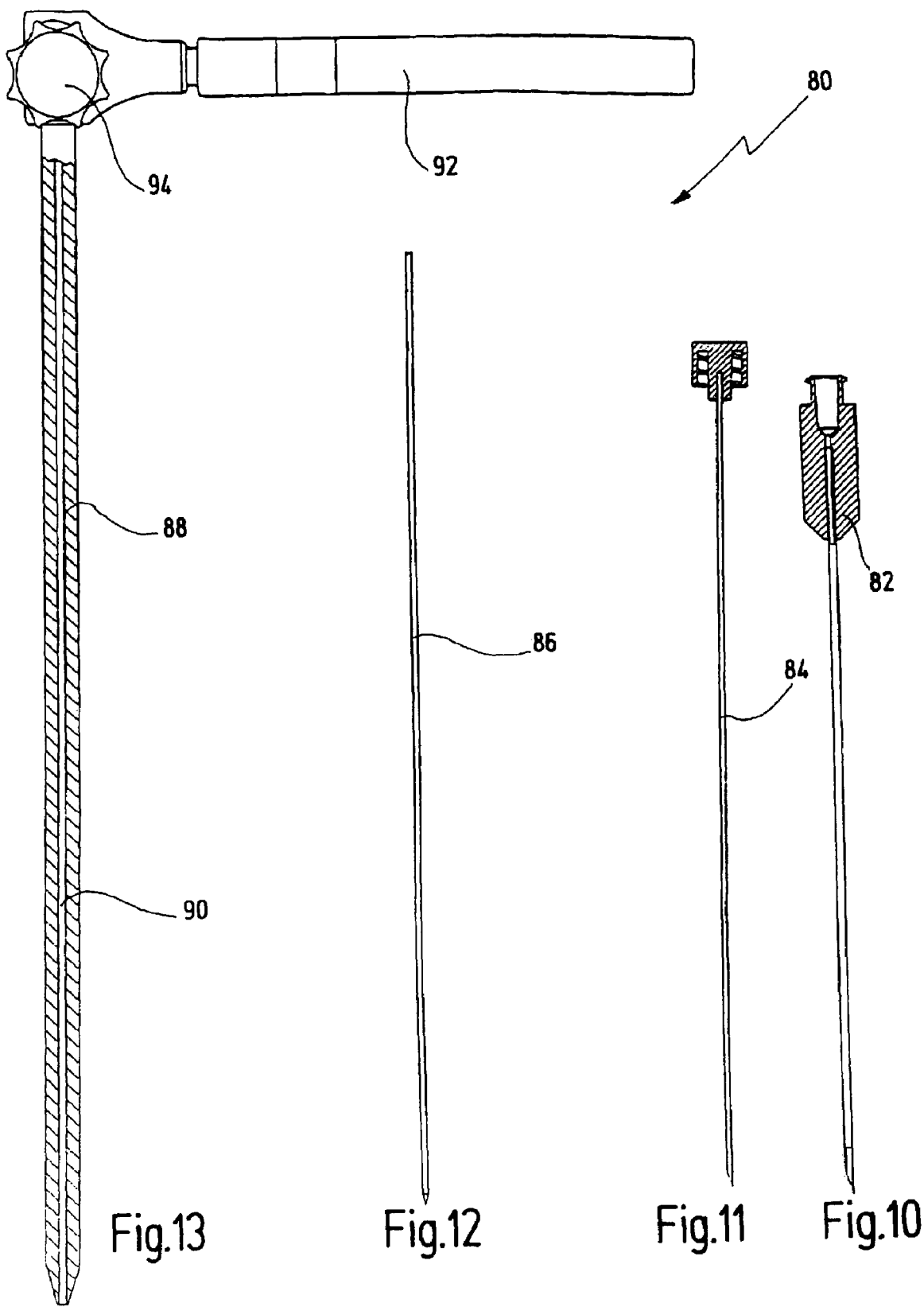
FIG. 10 shows a puncture needle of a dilatation device.
FIG. 11 shows an inner part of the puncture needle from FIG. 10.
FIG. 12 shows a guide wire which can be pushed into the puncture needle in FIG. 10.
FIG. 13 shows a dilatation mandrel and handle which can be pushed over the guide wire from FIG. 12.

FIGS. 10 to 14 show another possible use of the access cannula 10 according to the invention, involving an access for an arthroscopic operation, for example an operation on a shoulder joint. For this purpose, the puncture needle 82 shown in FIG. 10 is placed at the location where access is required between two bones of the joint. The diameter of the puncture needle 82 is extremely small and is in the range of approximately 1.5 mm.

The needle is advanced through the skin and into the joint until the needle tip can be detected by an arthroscope.

An inner part 84 extends through the puncture needle 82 which is designed as a hollow needle.

After inserting the puncture needle 82 into the joint, the inner part 84 is removed and a guide wire 86 is pushed fully into the puncture needle 82.

The puncture needle 82 is then removed, and the guide wire 84 now extends in the body or joint.

After making a skin incision, a dilatation mandrel 88 is placed on the guide wire 86 and for this purpose, as is shown in FIG. 13, is connected to a hand grip 92. The connection between hand grip 92 and dilatation mandrel 88 is effected via a locking screw 94. Depending on the expansion diameter which is desired, one or more dilatation mandrels 88 of ever increasing diameter are pushed on.

In the illustrative embodiment shown, only the dilatation mandrel 88 is initially pushed onto the guide wire 86 and pressed into the joint, this being made easier by the conical tip of the dilatation mandrel 88.

The external diameter of the dilatation mandrel 88 corresponds to the clear internal diameter of a sleeve 76 of a mandrel 72 which is in turn inserted into the tube 16 of an access cannula 10 according to the invention.

Figure 14:
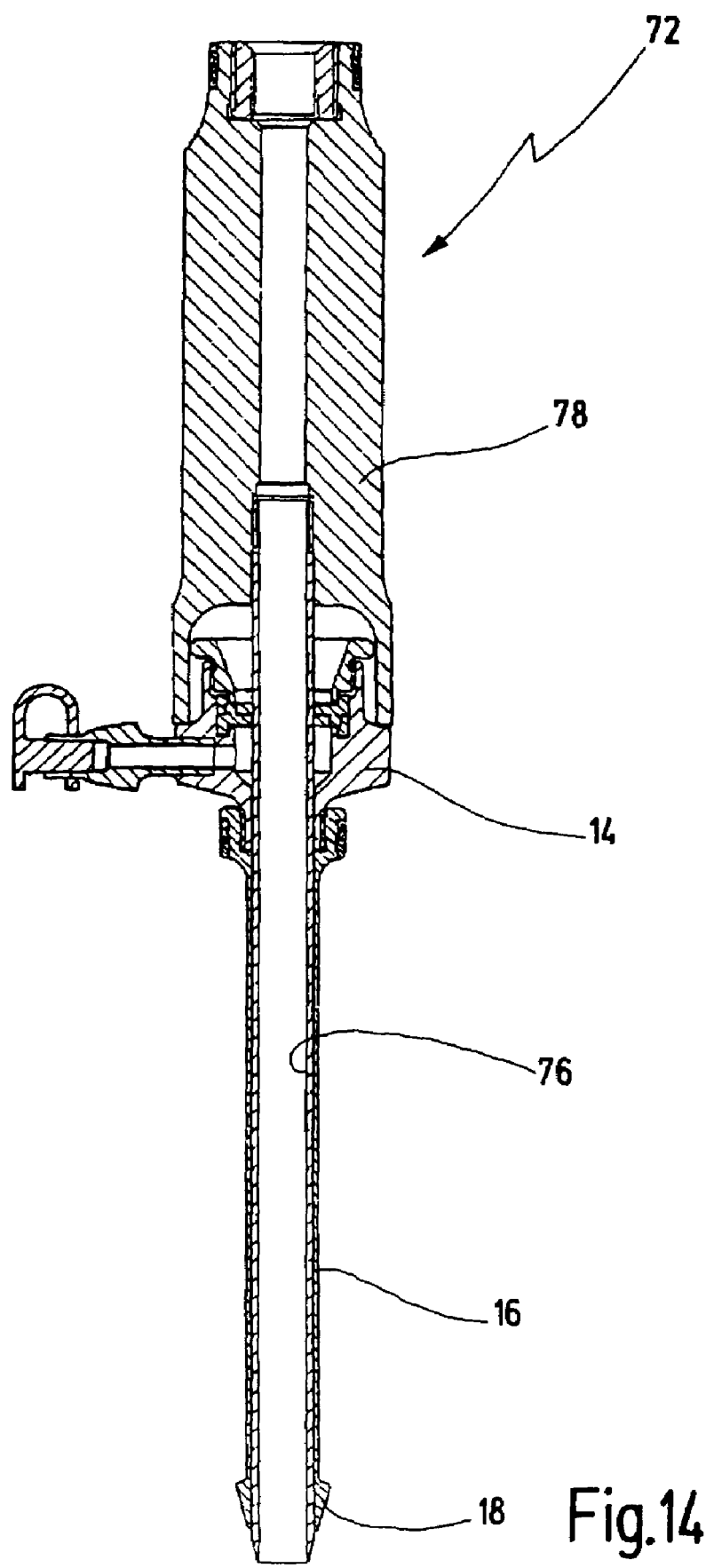
FIG. 14 shows an assembly consisting of the access cannula from FIGS. 1 and 6, with a mandrel from FIG. 7 inserted therein, so as to be pushed over the dilatation mandrel from FIG. 13.

This assembly is shown in FIG. 14.

After placement of the dilatation mandrel 88, the hand grip 92 is removed by releasing the locking screw 94, and the assembly in FIG. 14 is pushed over the dilatation mandrel 88. The access cannula 10 is again pushed in until its conical ring 18 has snapped into or locked in the joint. To do this, considerable forces have to be applied, and the hand grip 78 makes it possible to do this safely in particular because of its easy-to-grip shape.

The dilatation mandrel 88 and the mandrel 72 are then removed, and only the access cannula 10 shown in FIG. 6 is left in the body. The actual surgical intervention can then be performed by guiding the appropriate instruments through the cannula.

What is claimed is:

1. An access cannula for endoscopic operations, comprising a cannula tube, a valve body unit having a valve housing and a valve mounted in said valve housing, said valve body unit is connected releasably as a completely assembled valve body unit to one end of said cannula tube, said valve of said valve body unit ensures a tight closure of said cannula tube at said one end but allows an instrument to be passed through said valve body unit and said cannula, wherein said valve is designed as a double-disk valve having a first and a second disk, said first and second disks being connected to one another via an elastic, strip-like bridge, wherein said first and second disks are superimposed one to another with the elastic, strip-like bridge bent to form a loop extending laterally therefrom, and wherein said valve is a one-component part.

2. The access cannula of claim 1, wherein said valve housing is designed as a sterilizable component which can be used a number of times.

3. The access cannula of claim 1, wherein a slit seal is provided in each of said first and second disks of said double-disk valve.

4. The access cannula of claim 3, wherein said slits of said slit seal are designed in a star shape, and wherein said slits of said first and second disks of said double-disk valve are offset in relation to one another.

5. The access cannula of claim 1, wherein locking means are provided on said first and second disks and serve for locking said first and second disks one to another.

6. The access cannula of claim 1, wherein said cannula tube has, at its distal end, a ring, which widens conically in a proximal direction.

7. The access cannula of claim 1, wherein said cannula tube is designed as a component of a trocar device.

8. The access cannula of claim 7, wherein said trocar device has a mandrel with a hand grip, and a core rod, which mandrel can be introduced into said cannula tube.

9. The access cannula of claim 1, wherein said cannula tube is designed as a component of a dilatation device.

10. The access cannula of claim 9, wherein said dilatation device having a puncture needle, a guide wire, and at least one dilatation mandrel for attachment onto said guide wire, said cannula tube being designed in such a way that it can be pushed onto a dilatation mandrel.

11. The access cannula of claim 10, wherein said cannula tube can be pushed onto said dilatation mandrel by means of a mandrel provided with a hand grip.

12. The access cannula of claim 1, wherein said cannula tube is designed as a disposable component.

13. The access cannula of claim 1, wherein said valve housing is designed as a two-part housing, and wherein said valve is arranged between said two parts of said two-part valve housing.

14. The access cannula of claim 13, wherein a first part of said valve housing is provided by a main body having a neck for releasably connecting said valve housing to said cannula tube, and further has a recess into which said valve is inserted, said valve being fixed via a clamping ring providing a second part of said two-part valve housing.

* * * * *